United States Patent
Kumon et al.

(10) Patent No.: US 11,484,592 B2
(45) Date of Patent: Nov. 1, 2022

(54) COMBINATION THERAPY USING REIC/DKK-3 GENE AND A CHECKPOINT INHIBITOR

(71) Applicant: Momotaro-Gene Inc., Okayama (JP)

(72) Inventors: Hiromi Kumon, Okayama (JP); Richard Lowenthal, San Diego, CA (US)

(73) Assignee: MOMOTARO-GENE INC., Okayama (JP)

( * ) Notice: Subject to any disclaimer, the term of this patent is extended or adjusted under 35 U.S.C. 154(b) by 328 days.

(21) Appl. No.: 16/068,412

(22) PCT Filed: Jan. 6, 2017

(86) PCT No.: PCT/JP2017/000318
§ 371 (c)(1),
(2) Date: Jul. 6, 2018

(87) PCT Pub. No.: WO2017/119499
PCT Pub. Date: Jul. 13, 2017

(65) Prior Publication Data
US 2019/0015506 A1 Jan. 17, 2019

Related U.S. Application Data

(60) Provisional application No. 62/276,371, filed on Jan. 8, 2016.

(51) Int. Cl.
| | | |
|---|---|---|
| *A61K 39/395* | (2006.01) | |
| *A61K 45/06* | (2006.01) | |
| *C07K 16/28* | (2006.01) | |
| *A61P 35/00* | (2006.01) | |
| *C12N 15/861* | (2006.01) | |
| *A61K 39/00* | (2006.01) | |

(52) U.S. Cl.
CPC ...... *A61K 39/39558* (2013.01); *A61K 39/395* (2013.01); *A61K 45/06* (2013.01); *A61P 35/00* (2018.01); *C07K 16/2815* (2013.01); *C07K 16/2818* (2013.01); *C07K 16/2827* (2013.01); *C12N 15/861* (2013.01); *A61K 2039/505* (2013.01); *A61K 2039/545* (2013.01); *A61K 2300/00* (2013.01); *C07K 2317/76* (2013.01); *C12N 2710/10343* (2013.01)

(58) Field of Classification Search
None
See application file for complete search history.

(56) References Cited

U.S. PATENT DOCUMENTS

| | | | | |
|---|---|---|---|---|
| 8,618,273 B2* | 12/2013 | Kumon | ................ | C07K 16/18 536/23.5 |
| 8,658,611 B2* | 2/2014 | Kumon | .............. | C07K 14/4747 514/44 R |
| 8,658,612 B2* | 2/2014 | Kumon | ................ | C07K 14/47 514/44 R |
| 8,946,173 B2* | 2/2015 | Kumon | ................ | A61K 31/713 514/44 R |
| 9,222,107 B2* | 12/2015 | Kumon | .............. | A61K 38/1709 |
| 9,475,865 B2* | 10/2016 | Kumon | ................ | A61P 35/00 |
| 9,493,776 B2* | 11/2016 | Kumon | ................ | C12P 21/02 |
| 9,644,013 B2* | 5/2017 | Kumon | ................ | A61P 43/00 |
| 10,071,126 B2* | 9/2018 | Kumon | ................ | C12N 15/09 |
| 2006/0275263 A1 | 12/2006 | Namba et al. | | |
| 2009/0005538 A1 | 1/2009 | Kumon et al. | | |
| 2011/0269824 A1* | 11/2011 | Kumon | ................ | A61P 35/02 514/44 R |
| 2012/0034251 A1 | 2/2012 | Kumon et al. | | |
| 2015/0202290 A1 | 7/2015 | Vanderwalde et al. | | |

FOREIGN PATENT DOCUMENTS

| | | |
|---|---|---|
| CN | 104704002 A | 6/2015 |
| EP | 2 508 603 A1 | 10/2012 |
| WO | WO 01/38528 A1 | 5/2001 |
| WO | WO-2006/098074 A1 | 9/2006 |
| WO | WO 2015/069770 A1 | 5/2015 |
| WO | WO 2015/092382 A1 | 6/2015 |

OTHER PUBLICATIONS

Rios-Doria (Neoplasia Aug. 2015 17:661-670) (Year: 2015).*
Yang et al. (Nutrients Dec. 5, 2019, 11, 2979, doi: 10.3390/nu11122979) (Year: 2019).*
Kawasaki et al., "REIC/Dkk-3 overexpression downregulates P-glycoprotein in multidrug-resistant MCF7/ADR cells and induces apoptosis in breast cancer," Cancer Gene Therapy, online Jul. 25, 2008, 2009, 16(1):65-72.
Supplementary European Search Report dated Jul. 17, 2019, in EP 17736036.9.
Office Action dated Aug. 1, 2019, in Singapore application 11201805556Q.
Grasselly et al., "The Antitumor Activity of Combinations of Cytotoxic Chemotherapy and Immune Checkpoint Inhibitors Is Model-Dependent," Frontiers in Immunology 2018, Oct. 9, 2018, 9:2100, 13 pages.
Kawasaki et al., "REIC/Dkk-3 overexpression downregulates P-glycoprotein in multidrug-resistant MCF7/ADR cells and induces apoptosis in breast cancer," Cancer Gene Therapy, online Jul. 25, 2008, 2019, 16(1):65-72.
Kawauchi et al., "Preclinical Safety and Efficacy of in Situ REIC/Dkk-3 Gene Therapy for Prostate Cancer," Acta Med. Okayama, Jan. 1, 2012, 66(1):7-16.
Kumon et al., "Ad-REIC Gene Therapy: Promising Results in a Patient with Metastatic CRPC Following Chemotherapy," Clin. Med. Insights Oncol., Feb. 14, 2015, 9:31-38.

(Continued)

*Primary Examiner* — Peter J Reddig
(74) *Attorney, Agent, or Firm* — Foley & Lardner LLP

(57) ABSTRACT

An object of the present invention is to provide a method of treating cancer using a checkpoint inhibitor in combination with REIC/Dkk-3 gene. The present invention is a combination pharmaceutical kit for treating cancer comprising REIC/Dkk-3 in combination with a check point inhibitor and a method for treating cancer by administering REIC/Dkk-3 gene and a check point inhibitor to a cancer patient.

2 Claims, 5 Drawing Sheets
Specification includes a Sequence Listing.

(56) References Cited

OTHER PUBLICATIONS

International Search Report dated Feb. 14, 2017, in PCT/JP2017/000318.
Office Action dated Aug. 27, 2020 in RU 2018124802.
Shimazu et al., "Integrin antagonist augments the therapeutic effect of adenovirus-mediated REIC/Dkk-3 gene therapy for malignant glioma," Gene Therapy, 2015, 22:146-154.
Brahmer et al., "Safety and Activity of Anti-PD-L1 Antibody in Patients with Advanced Cancer," N. Engl. J. Med., Jun. 28, 2012, 366(26):2455-2465.
Office Action dated Jul. 21, 2021 in CN 201780004616.8.
Office Action dated Sep. 20, 2021 in RU 2021113516.

* cited by examiner

Fig. 2 pshuttle- REIC-TSC

```
     (1)          (2)
XbaI-REIC-KpnI-3xenh-EcoRI
```

T/CTAGAGCaccatgcagcggcttggggccaccctgctgtgcctgctgctggcggcggcggt (1)
cccacggccccgcgcccgctccgacggcgacctcggctccagtcaagcccggcccggctc
tcagctacccgcaggaggaggccacccTcaatgagatgttccgcgaggttgaggaactgatg
gaggacacgcagcacaaattgcgcagcgcggtggaagagatggaggcagaagaagctgctgc
taaagcatcatcagaagtgaacctggcaaacttacctcccagctatcacaatgagaccaaca
cagacacgaaggttggaaataataccatccatgtgcaccgagaaattcacaagataaccaac
aaccagactggacaaatggtcttttcagagacagttatcacatctgtgggagacgaagaagg
cagaaggagccacgagtgcatcatcgacgaggactgtgggcccagcatgtactgccagtttg
ccagcttccagtacacctgccagccatgccggggccagaggatgctctgcacccgggacagt
gagtgctgtggagaccagctgtgtgtctgggtcactgcaccaaaatggccaccaggggcag
caatgggaccatctgtgacaaccagagggactgccagccggggctgtgctgtgccttccaga
gaggcctgctgttccctgtgtgcacacccctgcccgtggagggcgagctttgccatgacccc
gccagccggcttctggacctcatcacctgggagctagagcctgatggagccttggaccgatg
cccttgtgccagtggcctcctctgccagccccacagccacagcctggtgtatgtgtgcaagc
cgaccttcgtggggagccgtgaccaagatggggagatcctgctgcccagagaggtccccgat
gagtatgaagttggcagcttcatggaggaggtgcgccaggagctggaggacctggagaggag
cctgactgaagagatggcgctgggggagcctgcggctgccgccgctgcactgctgggaggg
aagagatttagGGGGTAC/CCCGGCtagatgactaacGTTTAAACCCGCTGATCAGCCTCGA
CTGTGCCTTCTAGTTGCCAGCCATCTGTTGTTTGCCCCTCCCCGTGCCTTCCTTGACCCTG
GAAGGTGCCACTCCCACTGTCCTTTCCTAATAAAATGAGGAAATTGCATCGCATTGTCTGAG
TAGGTGTCATTCTATTCTGGGGGGTGGGGTGGGCAGGACAGCAAGGGGGAGGATTGGGAAG
ACAATAGCAGGCATGCTGGGGATGCGGTGGCTCTATGGcggagtactgtcctccgcttccc (2)
acgtggcggagggactggggacccgggcacccgtcctgcccctTcaccttccagctccgcct
cctccgcgcggaccccgccccgtcccgacccctcccgggtccccggcccagccccctccggg
ccctcccagccccctcccttccTttccgcggccccgccctctcctcgcggcgcgagtttTGG
AAAGTCCCCAGGCTCCCCAGCAGGCAGAAGTATCCAAAGCATCCATCTCAATTAGTCAGCAA
CCAGGTGTGGAAAGTCCCCAGGCTCCCCAGCAGGCAGAAGTATCCAAAGCATCCATCTCAAT
TAGTCAGCAACCATAGTCCCGCCCCTAACTCCGCCCATCCCGCCCCTAACTCCGCCCAGTTC
CGCCCATTCTCCGCCCCATGGCTGACTAATTTTTTTTATTTATGCAGAGGCCGAGGCCGCCT
CTGCCTCTGAGCTATTCCAGAAGTAGTGAGGAGGCTTTTTGGAGGCCAAGGCTTTTGCAAA
AAGCTCcgttacataacttacggtaaatggcccgcctggctgaccgcccaacgacccccgcc
cattgacgtcaataatgacgtatgttcccatagtaacgccaatagggactttccattgacgt
caatgggtggagtatttacggtaaactgcccacttggcagtacatcaagtgtatcatatgcc
aagtacgccccctattgacgtcaatgacggtaaatggcccgcctggcattatgcccagtaca
tgaccttatgggactttcctacttggcagtacatctacgtattagtcatcgctattaccatg
gtgatgcggttttggcagtacatcaatgggcgtggatagcggtttgactcacggggatttcc
aagtctccaccccattgacgtcaatgggagtttgttttggcaccaaaatcaacgggactttc
caaaatgtcgtaacaactccgccccattgacgcaaatgggcggtaggcgtgTTGCCGG/AAT
TC (SEQ ID NO:6)

= p < 0.01; ** = p < 0.001

COMBINATION THERAPY USING REIC/DKK-3 GENE AND A CHECKPOINT INHIBITOR

TECHNICAL FIELD

The present invention relates to a combination therapy for treatment of cancer using REIC/Dkk-3 gene and a checkpoint inhibitor.

BACKGROUND

REIC/Dkk-3 gene is known to be a gene relating to cell immortalization. It has been reported that the expression of this gene is suppressed in cancer cells. It has also been reported that the REIC/Dkk-3 gene has been used for cancer therapy (Patent Document 1).

A check point inhibitor such as anti-PD-1 (Programmed cell death 1) antibody, anti-PD-L1 (Programmed cell-death ligand 1), and the like are known to be useful for various malignant tumors.

CITATION LIST

Patent Literature

[PTL 1]
International Patent Publication WO01/038528

SUMMARY OF INVENTION

Technical Problem

An object of the present invention is to provide a method of treating cancer using a checkpoint inhibitor in combination with REIC/Dkk-3 gene.

Solution to Problem

The present inventors have examined the effect of the combination use of REIC/Dkk-3 and a checkpoint inhibitor for the treatment of cancers.

The present inventors found that the combination use of REIC/Dkk-3 and a checkpoint inhibitor enhances a systemic T cell response and anti-tumor responses. It indicates that the combination use of REIC/Dkk-3 and a checkpoint inhibitor is useful method for treating cancer.

Specifically, the present invention is as follows.

[1] A combination pharmaceutical kit for treating cancer comprising REIC/Dkk-3 in combination with a check point inhibitor.

[2] The combination pharmaceutical kit of [1], wherein the check point inhibitor is an anti-PD-1 antibody or anti-PD-L1 antibody.

[3] The combination pharmaceutical kit of [1], wherein an adenovirus vector comprising REIC/Dkk-3 gene is comprised.

[4] The combination pharmaceutical kit of [1], wherein the cancer is a prostate cancer.

[5] A method for treating cancer by administering REIC/Dkk-3 gene and a check point inhibitor to a cancer patient.

[6] The method for treating cancer of [5], wherein the check point inhibitor is an anti-PD-1 antibody or anti-PD-L1 antibody.

[7] The method for treating cancer of [5], wherein an adenovirus vector comprising REIC/Dkk-3 gene is administered.

[8] The method for treating cancer of [5], wherein the cancer is a prostate cancer.

[9] A method for combining REIC/Dkk-3 with a check point inhibitor to treat cancer.

[10] The method according to [9], wherein the check point inhibitor is an anti-PD-1 antibody or an anti-PD-L1 antibody.

[11] The method according to [9], wherein the check point inhibitor is an anti-PD-1 antibody.

[12] The method according to [9], wherein the check point inhibitor is an anti-PD-L1 antibody.

[13] Use of anti-PD-1 and anti-PD-L1 antibodies to manipulate the immune system such that cancer expresses PD-1 and PD-L1 on the cell surface making it susceptible to REIC/Dkk-3 gene (REIC/Dkk-3-induced anti-tumor immunity; CTLs induced by REIC/Dkk-3).

[14] A method for combining REIC/Dkk-3 with a check point inhibitor in the manufacture of a medicine to treat cancer.

[15] The method according to [14], wherein the check point inhibitor is an anti-PD-1 antibody or an anti-PD-L1 antibody.

Advantageous Effects of Invention

REIC/Dkk-3 gene and the checkpoint inhibitor have synergy effect in treating cancers.

BRIEF DESCRIPTION OF DRAWINGS

FIG. 2 shows the sequence of Ad-REIC/Dkk-3.

Figure 1:
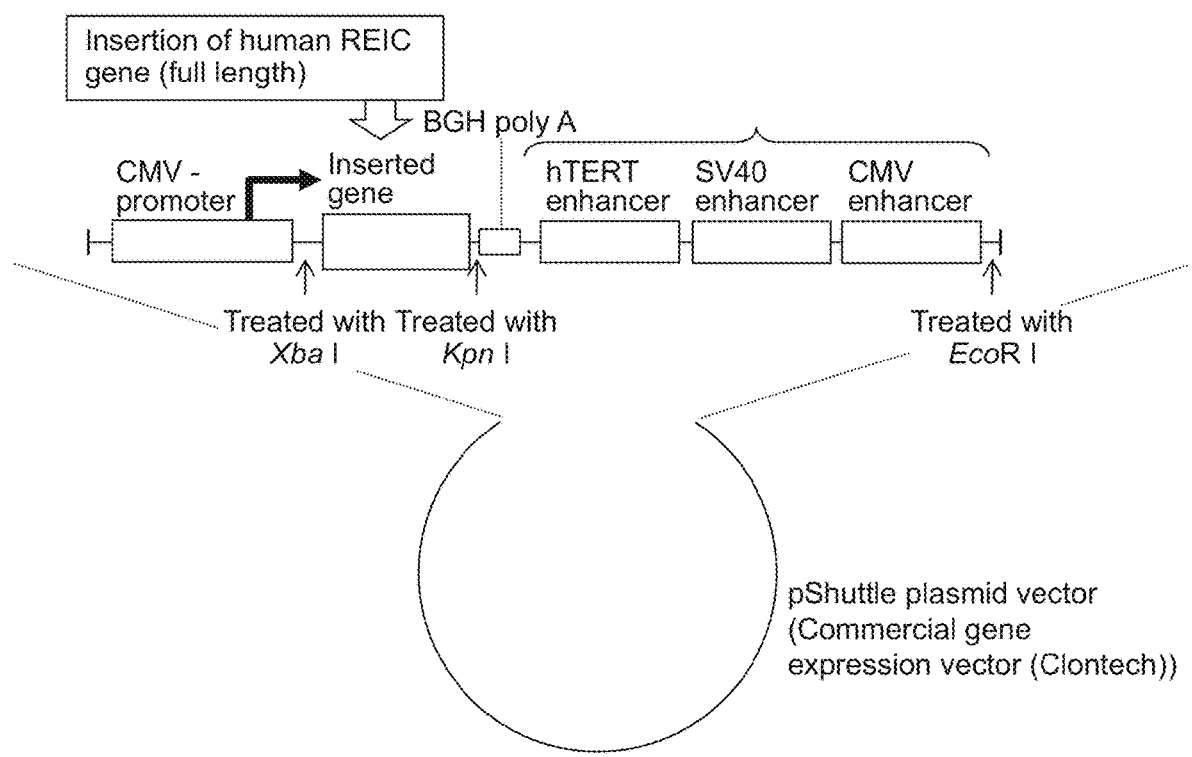
FIG. 1 shows an example of the structure of Ad-REIC/Dkk-3.

The present specification incorporates the contents described in the specification and drawings of U.S. Provisional Application No. 62/276,371 based on which the priority of the present application is claimed.

DETAILED DESCRIPTION OF THE PRESENT INVENTION

The combination therapy of the present invention uses a checkpoint inhibitor in combination with a REIC/Dkk-3 gene.

A checkpoint inhibitor includes anti-PD-1 (Programmed cell death 1) antibody, anti-PD-L1 (Programmed cell-death ligand 1), and the like.

The nucleotide sequence of REIC/Dkk-3 gene DNA is shown in SEQ ID NO: 1 of the sequence listing. Furthermore, the amino acid sequence of the REIC that is encoded by REIC/Dkk-3 DNA is shown in SEQ ID NO: 2 of the sequence listing. DNA having at least 85%, preferably at least 90%, further preferably at least 95%, and particularly preferably at least 97% sequence identity with the nucleotide sequence shown in SEQ ID NO: 1, when calculated using BLAST (Basic Local Alignment Search Tool) at the National Center for Biological Information (NCBI) or the like (with the use of, for example, default (i.e., initial) parameters) is included in REIC/Dkk-3 DNA.

A fragmental nucleotide of REIC/Dkk-3 can also be used. Examples of such a nucleotide comprising a nucleotide sequence ranging from the 1$^{st}$ nucleotide to any single nucleotide from the 117$^{th}$ to the 234$^{th}$ nucleotides in the nucleotide sequence of REIC/Dkk-3 DNA shown in SEQ ID NO: 1 include the polynucleotide (SEQ ID NO: 3) ranging from the 1$^{st}$ to the 117$^{th}$ nucleotides and the polynucleotide (SEQ ID NO: 4) ranging from the 1$^{st}$ to the 234$^{th}$ nucleotides.

The REIC/Dkk-3 gene can be introduced into a subject in accordance with a conventional technique. Examples of techniques for introducing a gene into a subject include a method involving the use of a virus vector and a method involving the use of a non-virus vector.

The REIC/Dkk-3 gene can be introduced into a cell or tissue using a recombinant expression vector into which a gene expression vector, such as a plasmid vector, has been incorporated, without the use of the above viruses.

Representative examples of virus vectors used for gene introduction include an adenovirus vector, an adeno-associated virus vector, and a retrovirus vector. A target gene may be introduced into a cell by introducing a target gene into a DNA or RNA virus, such as a detoxicated retrovirus, herpes virus, vaccinia virus, poxvirus, poliovirus, Sindbis virus, Sendai virus, SV40, or human immunodeficiency virus (HIV), and infecting the cell with such recombinant virus. An adenovirus vector is preferably used.

The vector comprises a construct comprising REIC/Dkk-3 gene. The construct comprising REIC/Dkk-3 DNA may adequately comprise a promoter or enhancer for transcribing the gene, poly A signal, a marker gene for labeling and/or selecting the cell into which the gene has been introduced, and the like. In such a case, a known promoter can be used.

The construct has a structure in which a DNA construct contains the REIC/Dkk-3 gene and a poly A addition sequence that are located downstream of at least a 1$^{st}$ promoter, and an enhancer or a 2$^{nd}$ promoter is ligated downstream of the DNA construct.

A promoter is a specific nucleotide sequence on DNA for initiation of transcription with the DNA as a template, and generally has a common sequence. For example, prokaryotes such as *Escherichia coli* generally has a TATAATG sequence at a 10-base-pair site that is a transcription initiation site, and a TTGACA sequence at a 35-base-pair site. Furthermore, eukaryotes generally have a TATA box at a 20-base-pair site. The expression cassette of the present invention may always have a 1$^{st}$ promoter at a site upstream of a gene to be expressed and may have a 2$^{nd}$ promoter at a site downstream of the gene to be expressed. These promoters to be used as the 1$^{st}$ promoter and the 2$^{nd}$ promoter are not limited and the 1$^{st}$ promoter and the 2$^{nd}$ promoter may be the same or different from each other. Non specific promoters that can accelerate the expression of foreign genes in all cells or tissues, tissue- or organ-specific promoters, tumor-specific promoters, and specific or selective promoters such as development- or differentiation-specific promoters can also be used herein. For example, a specific promoter can be used as the 1$^{st}$ promoter and a non specific promoter can be used as the 2$^{nd}$ promoter. Promoters to be used in the present invention are as follows. Examples of a cancer- or tumor-specific promoter include hTERT (human telomerase reverse transcriptase), PSA (prostate-specific antigen), c-myc, and a GLUT promoter. Examples of an ES cell- or cancer stem cell-specific promoter include OCT3/4 and NANOG promoters. An example of a neural stem cell-specific promoter is a Nestin promoter. Examples of a cell stress sensitive promoter include HSP70, HSP90, and p53 promoters. An example of a hepatocyte-specific promoter is an albumin promoter. An example of a radiosensitive promoter is a TNF-alpha promoter. An example of a promoter for increasing the number of copies of an infection plasmid is a SV40 promoter and the like. An example of a proliferative cell-specific promoter is an EF1-alpha promoter. Further specifically, for example, as the 1$^{st}$ promoter, a CMV-i promoter (hCMV+intron promoter), a b actin promoter, a CAG promoter, a CMV promoter, or the like is used and as the 2$^{nd}$ promoter, a CMV promoter or the like is used. Animal species from which a b actin promoter is derived is not limited. Mammalian b actin promoters such as a human b actin promoter and a chicken actin promoter are used. Furthermore, an artificial hybrid promoter such as the above CMV-i promoter can also be used. The CMV-i promoter can be synthesized based on the disclosure in the specification of U.S. Pat. No. 5,168,062 or the specification of U.S. Pat. No. 5,385,839. As such a promoter, a core promoter portion consisting of a minimum sequence having promoter activity may be used. The term "core promoter" refers to a promoter region capable of functioning to result in precise transcription initiation, which may contain a TATA box. Among the above promoters, a cancer- and/or tumor-specific promoter such as an hTERT promoter can be preferably used for cancer-targeting gene therapy or diagnosis of cancer with the use of gene expression.

Examples of the origin of the polyA addition sequence (polyadenylation sequence, polyA) include, but are not limited to, a growth hormone gene-derived polyA addition sequence (e.g., a bovine growth hormone gene-derived polyA addition sequence (BGA polyA), a human growth hormone gene-derived polyA addition sequence, an SV40 virus-derived polyA addition sequence, and a human or rabbit b globin gene-derived polyA addition sequence. Transcriptional efficiency is increased by causing the DNA construct to contain such a polyA addition sequence. A nucleotide sequence of BGA polyA addition sequence is shown as the 13$^{th}$ nucleotide and nucleotides following thereto of nucleotide sequence shown in SEQ ID NO: 5.

Examples of an enhancer are not limited, as long as it results in an increased amount of messenger RNA (mRNA) generated by transcription. An enhancer is a nucleotide sequence having an effect of accelerating the action of a promoter and generally has a length of around 100 bp in most cases. An enhancer can accelerate transcription regardless of the direction of the relevant sequence. One type of enhancer can be used in the present invention. Specifically, two or more (a plurality of) same enhancers may be used or a plurality of different enhancers may be used in combination. Also, when a plurality of different enhancers are used, the order thereof is not limited. For example, a CMV enhancer, an SV40 enhancer, an hTERT (Telomerase Reverse Transcriptase) enhancer, and the like can be used. An example thereof is a product resulting from linking of the hTERT enhancer, the SV40 enhancer, and the CMV enhancer in such order.

Moreover, a plurality of enhancers (e.g., 1 to 4 enhancers) may be ligated upstream of a DNA construct comprising DNA encoding a protein to be expressed and a poly A addition sequence. Enhancers to be ligated upstream thereof are not limited, and a CMV enhancer is preferable. An example thereof is 4×CMV enhancer prepared by linking four CMV enhancers.

When an enhancer is inserted immediately downstream of a DNA construct consisting of "promoter—gene to be expressed—poly A addition sequence," the protein of the gene (to be expressed more strongly) can be expressed than that in the case of a general conventional gene expression system.

In particular, through the use of a combination of a CMV i promoter and a CMV enhancer, in almost all cells (host cells), strong protein expression of a gene to be expressed becomes possible regardless of the type of transfection reagent used herein, although any gene is inserted.

Furthermore, RU5' may be ligated immediately upstream of DNA encoding a protein to be expressed. The expression " . . . (to a site) immediately upstream of" means that the relevant sequence is directly ligated via no other elements having specific functions. However, a short sequence may be contained between them, as a linker. RU5' is HTLV-derived LTR and is an element that increases protein expression through insertion thereof (Mol. Cell. Biol., Vol. 8 (1), p. 466-472, 1988). Insertion of RU5' in a direction opposite to that reported previously may cancel the promoter's effect of enhancing expression due to enhancer insertion.

Furthermore, UAS may be ligated to a site immediately upstream of an enhancer and/or a promoter. UAS is a binding region for a GAL4 gene. Insertion of a GAL4 gene into a site downstream of UAS can result in increased protein expression.

Moreover, SV40-ori may be ligated to the most upstream portion of the expression cassette. SV40-ori is a binding region for an SV40 gene. Insertion of an SV40 gene into a site downstream of SV40-ori results in increased protein expression.

Each of the above elements should be functionally ligated. Here, the term "functionally ligated" means that each element is ligated so that it can exhibit its functions and thus the expression of a gene to be expressed is enhanced.

Specifically, the DNA construct is prepared by ligating a CMV (cytomegarovirus) promoter to a site upstream of REIC/Dkk-3 DNA, and a polyA addition sequence (polyadenylation sequence, polyA) to a site downstream of REIC/Dkk-3 DNA. Moreover, enhancers (3×enh) prepared by linking an hTERT (Telomerase Reverse Transcriptase) enhancer, an SV40 enhancer, and a CMV (cytomegarovirus) enhancer in this order are ligated to a site downstream of the polyA addition sequence. Specifically, the DNA construct is prepared by ligating, from the 5' terminal side, (i) a CMV promoter, (ii) REIC/Dkk-3 DNA, (iii) a polyA addition sequence, and (iv) enhancers prepared by linking the hTER (Telomerase Reverse Transcriptase) enhancer, the SV40 enhancer, and the CMV enhancer in this order.

The structure of a portion of the DNA construct containing REIC/Dkk-3 DNA of the present invention, which lacks the CMV promoter, is shown in FIG. 2, and the sequence thereof is shown in SEQ ID NO: 6. In FIG. 2, a BGA polyA sequence is contained between REIC/Dkk-3 DNA and 3×enh. The DNA construct containing REIC/Dkk-3 DNA of the present invention has a CMV promoter upstream (5' side) of the sequence shown in SEQ ID NO: 4. SEQ ID NO: 7 shows the nucleotide sequence of the region containing BGH poly A and three enhancers (contained in the above construct). In FIG. 2, portions (1) and (2) enclosed by frames in the nucleotide sequence indicate DNA encoding the REIC/Dkk-3 protein and the three enhancers (3×enh), respectively.

The above elements should be functionally linked (ligated) to each other. The expression used herein, "functionally linked (ligated) to each other" means that elements are linked or ligated to each other so that each element can exhibit its functions so as to enhance the expression of a gene to be expressed.

The above expression cassette can be obtained by inserting REIC/Dkk-3 DNA into a pShuttle vector (Clonetech) containing a foreign gene insertion site downstream of a commercial CMV promoter, and a BGA polyA sequence downstream of the insertion site, and then ligating an hTERT (Telomerase Reverse Transcriptase) enhancer, an SV40 enhancer, and a CMV enhancer in this order to a site downstream of the BGA polyA sequence.

The DNA construct comprising REIC/Dkk-3 DNA is:

[1] A DNA construct for the expression of REIC/Dkk-3 DNA, which is prepared by ligating, from the 5' terminal side:
  (i) a CMV promoter;
  (ii) the following REIC/Dkk-3 DNA:
    (a) DNA comprising the nucleotide sequence shown in SEQ ID NO: 1,
    (b) DNA having at least 90%, 95%, 97% or 98% sequence identity with the nucleotide sequence shown in SEQ ID NO:1,
  (iii) a polyA addition sequence; and
  (iv) enhancers prepared by linking an hTERT (Telomerase Reverse Transcriptase) enhancer, an SV40 enhancer, and a CMV enhancer in this order;

[2] The DNA construct according to [1] above, wherein the polyA addition sequence is a polyA addition sequence (BGA polyA) derived from a bovine growth hormone gene; and The DNA construct according to [1] or [2] above, containing the nucleotide sequence shown in SEQ ID NO: 6, wherein (ii) REIC/Dkk-3 DNA, (iii) the polyA addition sequence, and (iv) enhancers prepared by linking the hTERT (Telomerase Reverse Transcriptase) enhancer, the SV40 enhancer, and the CMV enhancer in this order, are ligated.

The DNA construct can be prepared according to the Descriptions of WO2011/062298, US2012-0309050, WO2012/161352 and US2014-0147917, which are incorporated herein by reference in their entirety.

According to the present invention, an adenovirus vector comprising REIC/Dkk-3 DNA is called "Ad-REIC" or "Ad-REIC/Dkk-3." A vector system containing the DNA construct above is referred as an SGE (Super Gene Expression) system. For example, an adenovirus vector containing a DNA construct that contains REIC/Dkk-3 DNA is referred to such as "Ad5-SGE-REIC/Dkk-3." FIG. 1 shows an example of the structure of Ad-REIC/Dkk-3 and FIG. 2 shows the sequence of Ad-REIC/Dkk-3.

The above adenovirus vector containing the DNA construct is obtained by preparing a recombinant adenovirus through introduction of the DNA construct into an adenovirus vector. Introduction of the DNA construct into an adenovirus can be performed by introducing the DNA construct in a pShuttle vector containing the DNA construct of the present invention into an adenovirus, for example.

An adenovirus vector is characterized in that: (1) it enables gene transfer into many types of cells; (2) it enables efficient gene transfer into even cells at the stationary phase; (3) it can be concentrated by centrifugation, and thus a high-titer virus (10-11 PFU/ml or more) can be obtained; (4) and it is suitable for direct gene transfer into in vivotissue cells.

As adenoviruses for gene therapy, the first generation adenovirus vector prepared by deleting the E1/E3 region (Miyake, S., et al., Proc. Natl. Acad. Sci. U.S.A., 93, 1320, 1996), the second generation adenovirus vector prepared by deleting, in addition to the E1/E3 region, the E2 or E4 region (Lieber, A., et al., J. Virol., 70, 8944, 1996; Mizuguchi, H. & Kay, M. A., Hum. Gene Ther., 10, 2013, 1999), and the third generation adenovirus vector prepared by almost completely deleting the adenovirus genome (GUTLESS) (Steinwaerder, D. S., et al., J. Virol., 73, 9303, 1999) have been developed. Any of these adenovirus vectors can be used without particular limitation for the gene transfer according to the present invention.

A recombinant adenovirus vector containing the DNA construct that contains REIC/Dkk-3 DNA is administered to a human subject or a subject that is another mammal, so that a gene for cancer therapy is delivered to cancer cells of the subject, the gene is expressed in cancer cells and, tumor cell growth is suppressed so that therapeutic effects are exhibited against cancer.

The adenovirus vector of the present invention can be administered by methods that can be used in the field of gene therapy, such as via intravascular administration (e.g., intravenous administration and intraarterial administration), peroral administration, intraperitoneal administration, intratracheal administration, intrabronchial administration, subcutaneous administration, or transdermal administration. In particular, the adenovirus vector of the present invention has strong directivity toward a specific tissue or cells, and thus is capable of efficiently delivering a target gene to a specific tissue or cells. Therefore, efficient diagnosis and treatment can be performed even through intravascular administration of the adenovirus vector.

The adenovirus vector may be administered at a therapeutically effective dose, which can be easily determined by persons skilled in the field of gene therapy. Furthermore, the dose can be adequately varied depending on the severity of the pathological condition, gender, age, body weight, lifestyle, and the like of the subject. For example, the adenovirus vector may be administered in doses ranging from $0.5 \times 10^{11}$ to $2.0 \times 10^{12}$ viral genome/kg body weight, preferably ranging from $1.0 \times 10^{11}$ to $1.0 \times 10^{12}$ viral genome/kg body weight, and further preferably ranging from $1.0 \times 10^{11}$ to $5.0 \times 10^{11}$ viral genome/kg body weight. The term "viral genome" represents the number of molecules of the genome of an adenovirus (viral particle count), and is also referred as "particle (s)." That is, the term "viral genome" is the same with the term "viral particles (vp)".

The checkpoint inhibitor such as anti-PD-1 (Programmed cell death 1) antibody and anti-PD-L1 (Programmed cell-death ligand 1) antibody functions as an immune checkpoint to down regulate the immune system by preventing the activation of T cells. The inhibitory effect of the checkpoint inhibitor is attained by promoting apoptosis (programmed cell death) in antigen specific T cells in lymph nodes and reduce apoptosis in reguratory T cells (Treg).

The checkpoint inhibitor can be administered in a known way. For example, the dose varies depending on symptoms, age, body weight, and other conditions. A dose of 0.001 mg to 100 mg may be administered at intervals of several days, several weeks, or several months via hypodermic injection, intramuscular injection, or intravenous injection.

The adenovirus vector or the checkpoint inhibitor contains a carrier, a diluent, and an excipient which are generally used in the field of formulation. For example, lactose, magnesium stearate, and the like are used as carriers or excipients for tablets. An aqueous solution is used for injection, such as physiological saline or an isotonic solution containing dextrose or another adjuvant, and this can be used in combination with an appropriate solubilizing agent (e.g., alcohol, polyalcohol such as propylene glycol, and nonionic surfactant). As an oily fluid, sesame oil, soybean oil, or the like is used. As a solubilizing agent, benzyl benzoate, benzyl alcohol, or the like can also be used in combination therewith.

REIC/Dkk-3 protein encoded by REIC/Dkk-3 gene can treat or prevent cancer by upregulating anti-cancer immune system. Further, it induces apoptosis of cancer cells. Specifically, REIC/Dkk-3 protein induces CTLs (cytotoxic T lymphocytes) and the CTLs attack cancer cells systemically. The cancer cells attacked by CTLs perform defense function and the cancer cells express PD-L1. The check point inhibitor inhibits the defense function of the cancer cells.

REIC/Dkk-3 gene alone enhances systemic CD8 T cell priming. Further, REIC/Dkk-3 gene alone induces PD-1 on the infiltrating CD8 T cells and presumably PD-L1 in the injected microenvironment. This serves to dampen CD8 (and tumor-specific) T cell expansion. Furthermore, REIC/Dkk-3 gene alone leads to higher levels of CD4 memory T cell exhaustion. Combining REIC/Dkk-3 gene to anti-PD-1 or anti-PD-L1 enhances a systemic T cell response and anti-tumor responses. This combination also induced M2 macrophages into the injected tumor microenvironment, which may dampen its overall efficacy. There were no differential effects on regulatory T cells (Tregs).

While REIC/Dkk-3 gene may induce adaptive resistance that blocks therapeutic efficacy, combinational therapy with PD-1 blockade can promote tumor inhibitory effects in murine prostate cancers. Combinational therapy (REIC/Dkk-3 gene with an check point inhibitor) can promote Spas-1+CD8 cells in both ipisilateral and contralateral tumors. However, combinational therapy had minimal effects on Treg cells. Although combinational therapy can overcome adaptive resistance, it may potentially recruit or increase tumor infiltrating myeloid cells.

REIC/Dkk-3 gene and the checkpoint inhibitor have synergy effect in treating cancers. Anti-PD-1 and anti-PD-L1 antibodies manipulate the immune system such that cancer expresses PD-1 and PD-L1 on the cell surface making it susceptible to REIC/Dkk-3 gene (REIC/Dkk-3-induced anti-tumor immunity; CTLs induced by REIC/Dkk-3). Combination use of REIC/Dkk-3 gene and the checkpoint inhibitor is more effective on the treatment of cancer than REIC/Dkk-3 gene alone or the checkpoint inhibitor alone.

REIC/Dkk-3 gene can be administered simultaneously, separately or sequentially with the administration of the checkpoint inhibitor. REIC/Dkk-3 gene can also be administered before or after the administration of the checkpoint inhibitor. Preferably, REIC/Dkk-3 gene is administered before the administration of the checkpoint inhibitor. When the checkpoint inhibitor is administered separately, the checkpoint inhibitor is administered 1 to 24 hours, 1 to 30 days before or after the administration of REIC/Dkk-3 gene. Further, the checkpoint inhibitor can be administered at the same interval with REIC/Dkk-3 gene. The checkpoint inhibitor is administered once when REIC/Dkk-3 gene is administered plural times. Alternatively, the REIC/Dkk-3 gene is administered once when the checkpoint inhibitor is administered plural times.

Examples of cancer to be treated herein include, but are not limited to, prostate cancer, brain/nerve tumor, skin cancer, gastric cancer, lung cancer, hepatic cancer, lymphoma/leukemia, colon cancer, pancreatic cancer, anal/rectal cancer, esophageal cancer, uterine cancer, breast cancer, adrenal cancer, kidney cancer, renal pelvic and ureteral cancer, bladder cancer, urethral cancer, penile cancer, testicular cancer, osteoma/osteosarcoma, leiomyoma, rhabdomyoma and mesothelioma.

The present invention also comprises a combination, combination preparation or combination pharmaceutical kit comprising REIC/Dkk-3 gene and a checkpoint inhibitor.

The present invention also comprises a method for combining REIC/Dkk-3 with a check point inhibitor in the manufacture of a medicine to treat cancer.

The present invention also comprises a pharmaceutical composition comprising a REIC/Dkk-3 and a check point inhibitor

EXAMPLES

Hereinafter, some embodiments will be described more specifically by way of Examples, but the embodiments not intended to be limited to the following Examples.

Efficacy of a combination of MTG-201 and a checkpoint inhibitor (anti-PD-1, anti-PD-L1 and anti-CTLA-4 antibodies) in a transgenic adenocarcinoma of mouse prostate (TRAMP) model 1. Summary The objective of this Example is to evaluate the potential immunologic effects and efficacy of MTG-201 (Ad5-SGE-REIC/Dkk-3) in combination with three checkpoint inhibitors; anti-PD1 and anti-CTLA-4 antibodies using the transgenic adenocarcinoma mouse prostate (TRAMP) model. The study evaluated the tumor growth and overall survival of intratumoral MTG-201 treatment alone and in combination with antibodies to CTLA4 and PD-1.

Following a single intratumoral injection of MTG-201 at a dose level of $5 \times 10^{10}$ vp per mouse there was a statistically significant decrease in tumor volume seen in the MTG-201+α-PD-1 group compared to the other treatment groups and controls ($p<0.01$) and a highly significant decrease compared to the ad-LacZ alone control ($p<0.001$). In addition, the overall survival of mice treated with MTG-201+α-PD-1 was a significantly higher compared to the other treatment groups and controls ($p<0.01$-$p<0.001$).

2. Introduction 2.1. Study Objective

The objective of this study is to evaluate the potential immunologic effects and efficacy of MTG-201 (Ad5-SGE-REIC/Dkk-3) in combination with three checkpoint inhibitors; anti-PD1, anti-PD-L1, and anti-CTLA-4 antibodies using the transgenic adenocarcinoma mouse prostate (TRAMP) model.

3. Dose Formulation and Preparation 3.1. Test Article and Vehicle

Test Article, vehicle and control used are as follows.

3.1.1. Test Article

Test Article Name: MTG-201 (Ad5-SGE-REIC/Dkk3)—a viral vector that includes a human transgene (Dikkopf-3 gene) that produces REIC protein when infecting target cells.

Storage Condition: Frozen (−60 to −90° C.) MTG-201 (Ad5-SGE-REIC/Dkk3) can be prepared according to the Descriptions of WO2011/062298, US2012-0309050, WO2012/161352 and US2014-0147917.

3.1.2. Vehicle

Vehicle Name: Tris Buffer/NaCl/pH 8.0/2.5% Glycerol

Tris Buffer/NaCl/pH 8.0/2.5% Glycerol 3.1.3. Control

Control Name: Ad-LacZ (adenovirus expressing β-galactosidase)

Storage Condition: Frozen (−60 to −90° C.)

4. Test Article Formulation 4.1. Preparation

The test article was supplied frozen. On the day of dosing, the test article was thawed and held on ice for up to 6 hours until dosing.

4.2. Concentration

Test article formulation concentrations were calculated based upon viral particles (vp) per mL. No adjustment will be made for purity. Prior to dosing, the test article was diluted with cold saline to achieve the desired dose concentrations (Table 1). The test article was not filtered. Fresh formulations were prepared for each concentration prior to use.

TABLE 1

Dilution Table

| Groups | Test Article Concentration | Injection Volume | Target Dose | Final Concentration |
|---|---|---|---|---|
| 1, 5-7, 8-9, 12-13 | $1.01 \times 10^{12}$ vp/mL | 50 µL | $5 \times 10^{10}$ vp | $1 \times 10^{12}$ vp |

4.3. Storage

Following preparation, the formulation was stored refrigerated (2 to 8° C.) or on wet ice.

4.4. Stability

It was confirmed that the test article was stable for the duration of dosing. The test article was use within 4 hours of thawing.

5. TEST SYSTEM 5.1. Species, Strain, and Supplier

Eighty-six (86) male C57BL/6 mice were obtained from Jackson Laboratories for use in this study. Seventy-eight (78) mice were used on study.

5.2. Specification

The mice were 8-9 weeks of age at arrival. Tumor will be injected at 8-10 weeks old mice. Mice will be treated with MTG at approximately 20 weeks old (based on tumor grow kinetics).

The mice weighed 20 to 30 g, as measured within 3 days of arrival. The actual range may have varied, but was documented in the data.

5.3. Husbandry

The mice were housed 5 per cage. Temperature and humidity was maintained as standard room temperature and humidity. Fluorescent lighting was provided via an automatic timer for approximately 12 hours per day. On occasion, the dark cycle may have been interrupted intermittently due to study-related activities.

Tap water was supplied ad libitum to all animals via an automatic water system unless otherwise indicated. The basal diet was PicoLab® Mouse Diet 20, product 5058, catalog #0007689, Lab Diet (St. Louis, Mo.). This diet was available ad libitum unless designated otherwise.

5.4. Justification of Test System

To investigate prostate cancer in mice, syngeneic transplantable prostate cancer cell lines were developed from prostate tumors that arose from transgenic adenocarcinoma mouse prostate (TRAMP) mice as a result of the expression of the SV40 large T antigen oncoprotein under a prostate-specific promoter. Dr. Fong's group has utilized this model to test immunotherapies for prostate cancer. These cell lines do not express the SV40 large T antigen in vitro or in vivo, making them suitable for immunotherapeutic studies. TRAMP cells were injected subcutaneously bilaterally (2 tumors/mouse; each tumor site contained $5 \times 10^5$ tumor cells) into the backs of male wild-type C57BL/6 mice, the syngeneic host for TRAMP cells. One of the tumors was then treated with either Ad-LacZ or MTG-201. In specified groups, mice were also treated with the combination of MTG-201 with each of two checkpoint inhibitors (anti-PD-1 and anti-CTLA-4 mouse antibody) 3 to 7 days after the treatment of Ad-LacZ or MTG-201. The study evaluated tumor growth and overall survival to intratumoral MTG-201 treatment alone and in combination with antibodies to CTLA4 and PD-1. For anti-CTLA-4 and anti-PD-1, the dosage will be 200 μg/mouse, intraperitoneally (IP).

6. Study Design 6.1. Xenographic Model

Survival groups: TRAMP-C2 cells ($5\times10^5$) were injected subcutaneously (1 tumor/mouse) into the backs of the male wild-type C57BL/6 mice, the syngeneic host for TRAMP cells.

Immune response groups: TRAMP-C2 cells ($5\times10^5$) were injected subcutaneously bilaterally (2 tumors/mouse) into the backs of the male wild-type C57BL/6 mice, the syngeneic host for TRAMP cells.

6.2. Group Assignment

The volume of each prostate tumor was allowed to reach ~150 mm³. Tumor-bearing mice were randomly assigned to the control or treatment groups (Table 2 and Table 3).

TABLE 2

Group Assignments - Survival Groups

| Group | Treatment | Number of Animals* |
|---|---|---|
| 1 | Ad-LacZ Control | 8 |
| 2 | MTG-201 | 8 |
| 3 | Anti-CTLA-4 | 8 |
| 4 | Ad-LacZ + anti-CTLA-4** | 8 |
| 5 | MTG-201 + anti-CTLA-4** | 8 |
| 6 | MTG-201 + anti-PD-1** | 8 |

*see Section 6.3.3. for sacrifice schedule
**checkpoint inhibitors (anti-PD-1 and anti-CTLA-4 mouse antibody) will be injected on Days 0 and 7 after the treatment of Ad-LacZ or MTC4-201.

Figure 3:
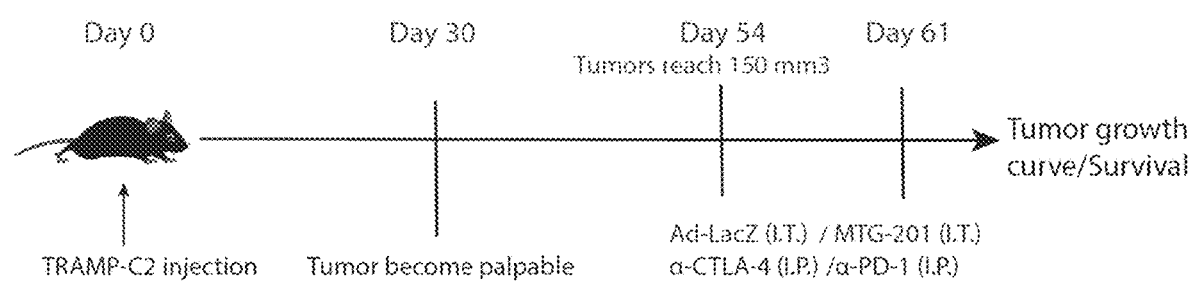
FIG. 3 shows the study schema for the survival groups of the Example.

The study schema for the survival groups is illustrated in FIG. 3.

TABLE 3

Group Assignments - Immune Response Groups

| Group | Treatment | Number of Animals Total | Sacrificed 15 days post antibody treatment |
|---|---|---|---|
| 7 | Ad-LacZ Control | 5 | 5 |
| 8 | MTG-201 | 5 | 5 |
| 9 | Anti-CTLA-4 | 5 | 5 |
| 10 | Ad-LacZ + anti-CTLA-4* | 5 | 5 |
| 11 | MTG-201 + anti-CTLA-4* | 5 | 5 |
| 12 | MTG-201 + anti-PD-1* | 5 | 5 |

*checkpoint inhibitors (anti-PD-1 and anti-CTLA-4 mouse antibody) were injected on Days 0 and 7 after the treatment of Ad-LacZ or MTG-201. Mice were harvested at Day 15.

6.3 Test Article and Vehicle Administration 6.3.1 Justification of Dose Level

The dose level was selected on the basis of available data from previous studies. This dose level is supported by three other GLP toxicology studies in the rat and dog. One study (1718-003) included Ad-SGE-REIC/Dkk-3 with injection into the prostate of a rate at the same dose as being used in this study ($5\times10^{10}$ vp/animal). The other two studies (1718-001 and 1718-002) were in the rat at the same doses and dog at a $1.0\times10^{12}$ vp dose with a similar viral vector that produced REIC protein (Ad-CAG-REIC/Dkk-3) where the promotor sequence was different.

6.3.1. Justification of Route of Administration

Injection into the tumor is one of the intended routes of administration in humans.

6.3.2. Administration

On Day 0, one of the tumors was treated with either Ad-LacZ, or MTG-201 by a direct injection into the tumor at a volume of 50 μL. $5\times10^{10}$ plaque-forming units of adenovirus vector (Ad-LacZ and MTG-201) adjusted to 0.05 mL volume with PBS buffer was injected intratumorally. Animals were anesthetized with isoflurane prior to injection.

In specified groups (Table 2 and Table 3), mice were also treated with anti-CTLA-4 mouse antibody, and the combination of MTG-201 with each of two checkpoint inhibitors (anti-PD-1 and anti-CTLA-4 mouse antibody) 0 and 7 days after the treatment of Ad-LacZ or MTG-201.

6.4. Study Evaluation 6.4.1 Cageside Observation

Mice were monitored 3 times a week and observed for morbidity, mortality, injury, and availability of food and water. Any animals in poor health were identified for further monitoring and possible euthanasia.

6.4.2. Tumor Growth Assessment

Tumors were measured and recorded every 3 to 4 days using calipers, and tumor volume were calculated using the formula V=0.52 (L*W*W), whereby V is volume, L is length (longer diameter) and W is width (shorter diameter).

6.5. Data Analysis

Individual data at the times specified are reported along with group mean values±standard errors.

7. STATISTICS

The raw data was tabulated within each time interval and the mean and standard deviation was calculated for each endpoint by group. For each endpoint, treatment groups were compared to the control group and each of the other treatment groups using the analysis outlined in Table 4.

When comparing two groups, unpaired Student's t test was performed for the statistical analysis and the difference was considered significant at $p<0.05$. For comparison among groups, one-way ANOVA with post-hoc Bonferroni correction was used.

TABLE 4

Statistical Comparisons

| Control Group | Comparison Groups | | | | | |
|---|---|---|---|---|---|---|
| Survival Groups | | | | | | |
| 1 | 2 | 3 | 4 | 5 | 6 | 7 |
| 2 | 1 | 3 | 4 | 5 | 6 | 7 |
| 3 | 1 | 2 | 4 | 5 | 6 | 7 |
| 4 | 1 | 2 | 3 | 5 | 6 | 7 |
| 5 | 1 | 2 | 3 | 4 | 6 | 7 |
| 6 | 1 | 2 | 3 | 4 | 5 | 7 |
| 7 | 1 | 2 | 3 | 4 | 5 | 6 |
| Immune Response Group | | | | | | |
| 8 | 9 | 10 | 11 | 12 | 13 | 14 |
| 9 | 8 | 10 | 11 | 12 | 13 | 14 |
| 10 | 8 | 9 | 11 | 12 | 13 | 14 |
| 11 | 8 | 9 | 10 | 12 | 13 | 14 |
| 12 | 8 | 9 | 10 | 11 | 13 | 14 |
| 13 | 8 | 9 | 10 | 11 | 12 | 14 |
| 14 | 8 | 9 | 10 | 11 | 12 | 13 |

The endpoints were as follows:

Experiment 1: tumor growth and overall survival. Mice with tumors that reached 300 mm³ were euthanized.

An estimate of the variance (Mean Square Error or MSE) within groups was computed from a one-way analysis of variance (ANOVA) with a Bonferroni correction. Control to treatment pair-wise comparisons was conducted using Student's t-test.

Results of all pair-wise comparisons were reported at the 0.05 and 0.01 significance levels. All endpoints were analyzed using two-tailed tests unless indicated otherwise.

8. RESULTS

8.1. Tumor Growth Assessment

Figure 4:
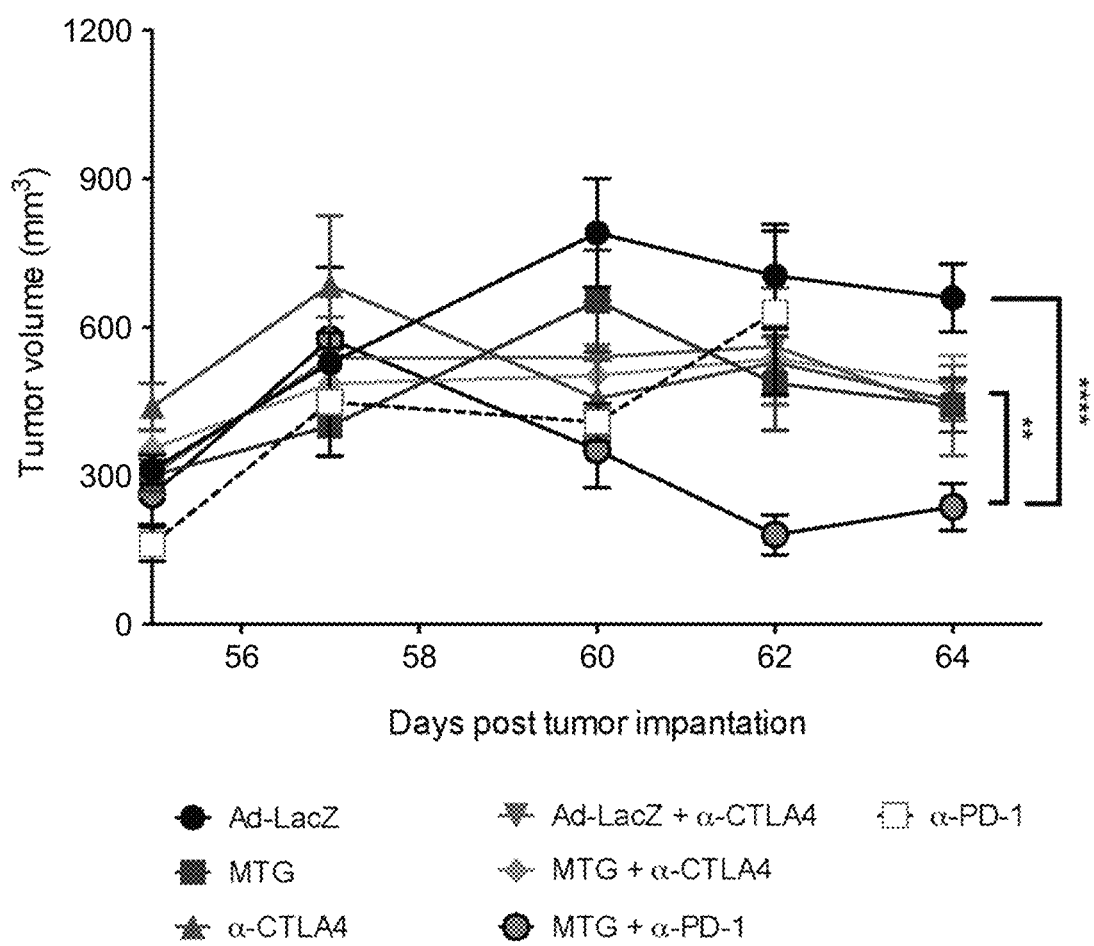
FIG. 4 shows the tumor growth post intratumoral MTG-201 treatment alone and in combination with antibodies to CTLA4 and PD-1.

Tumor growth post intratumoral MTG-201 treatment alone and in combination with antibodies to CTLA4 and PD-1 was evaluated. FIG. 4 shows the results. In FIG. 4, open square (□) shows anti-PD-1 (α-PD1) historical data which was generated by the same laboratory using the same mouse model. As seen in FIG. 4, there was a statistically significant decrease in tumor volume seen in the MTG-201+α-PD-1 group compared to the other treatment groups and controls ($p<0.01$) and a highly significant decrease compared to the ad-LacZ alone control ($p<0.001$). Further, there was a highly significant decrease in tumor volume seen in the MTG-201+α-PD-1 group compared to the α-PD-1 alone group. These results demonstrate that MTG-201+anti-PD-1 inhibits tumor growth.

8.2. Overall Survival

Figure 5:
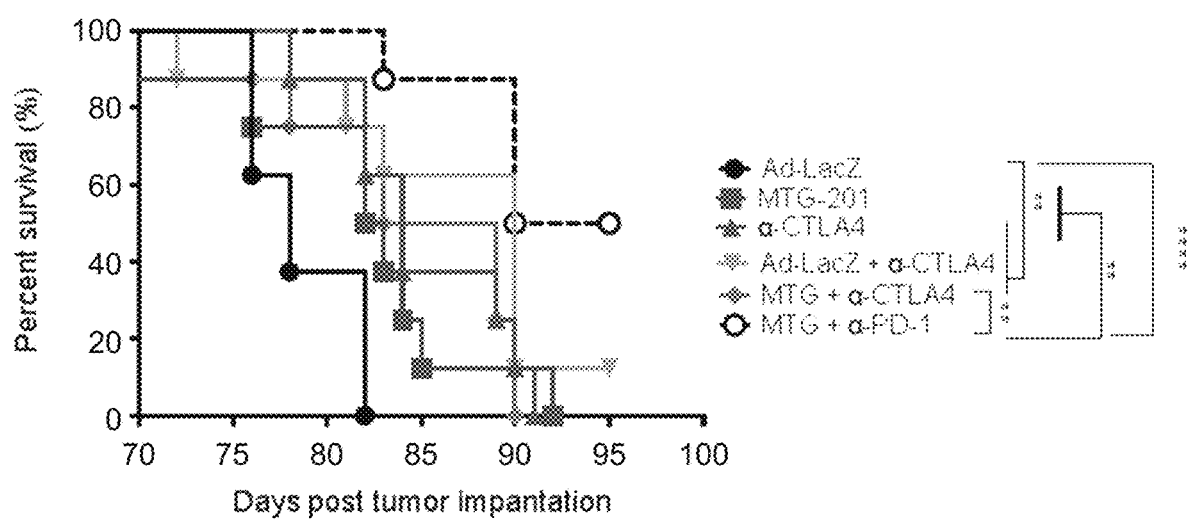
FIG. 5 shows the overall survival post intratumoral MTG-201 treatment alone and in combination with antibodies to CTLA4 and PD-1.

Overall survival post intratumoral MTG-201 treatment alone and in combination with antibodies to CTLA4 and PD-1 was evaluated. As seen in FIG. 5, the overall survival of mice in the MTG-201+α-PD-1 group was a significantly higher compared to the other treatment groups and controls ($p<0.01$-$p<0.001$). These results suggest that MTG-201+anti-PD-1 provide survival benefits.

9. Conclusion

The study evaluated the tumor growth and overall survival of intratumoral MTG-201 treatment alone and in combination with antibodies to CTLA4 and PD-1.

Following a single intratumoral injection of MTG-201 at a dose level of $5\times10^{10}$ vp per mouse there was a statistically significant decrease in tumor volume seen in the MTG-201+α-PD-1 group compared to the other treatment groups and controls ($p<0.01$) and a highly significant decrease compared to the ad-LacZ alone control ($p<0.001$). In addition, the overall survival of mice treated with MTG-201+α-PD-1 was a significantly higher compared to the other treatment groups and controls ($p<0.01$-$p<0.001$).

All publications, patents, and patent applications cited herein are incorporated herein by reference in their entirety.

The invention claimed is:

1. A combination pharmaceutical kit for treating prostate cancer consisting of as active ingredients an adenovirus vector comprising REIC/Dkk-3 gene in combination with an anti-PD-1 antibody, wherein the adenovirus vector comprising REIC/Dkk-3 gene comprises a DNA construct for the expression of REIC/Dkk-3 DNA, which is prepared by ligating, from the 5' terminal side:
   (i) a CMV promoter;
   (ii) REIC/Dkk-3 DNA;
   (iii) a polyA addition sequence; and
   (iv) enhancers prepared by linking an hTERT (Telomerase Reverse Transcriptase) enhancer, an SV40 enhancer, and a CMV enhancer in this order.

2. A method for treating prostate cancer by administering a combination pharmaceutical consisting of an adenovirus vector comprising REIC/Dkk-3 gene and an anti-PD-1 antibody as active ingredients to a prostate cancer patient, wherein the adenovirus vector comprising REIC/Dkk-3 gene comprises a DNA construct for the expression of REIC/Dkk-3 DNA, which is prepared by ligating, from the 5' terminal side:
   (i) a CMV promoter;
   (ii) REIC/Dkk-3 DNA;
   (iii) a polyA addition sequence; and
   (iv) enhancers prepared by linking an hTERT (Telomerase Reverse Transcriptase) enhancer, an SV40 enhancer, and a CMV enhancer in this order.

* * * * *

SEQUENCE LISTING

```
<160> NUMBER OF SEQ ID NOS: 9

<210> SEQ ID NO 1
<211> LENGTH: 1053
<212> TYPE: DNA
<213> ORGANISM: Homo sapiens
<220> FEATURE:
<221> NAME/KEY: CDS
<222> LOCATION: (1)..(1053)

<400> SEQUENCE: 1 atg cag cgg ctt ggg gcc acc ctg ctg tgc ctg cta ctg gcg gcg gcg        48
Met Gln Arg Leu Gly Ala Thr Leu Leu Cys Leu Leu Leu Ala Ala Ala
  1               5                  10                  15 gtc ccc acg gcc ccc gcg ccc gct ccg acg gcg acc tcg gct cca gtc        96
Val Pro Thr Ala Pro Ala Pro Ala Pro Thr Ala Thr Ser Ala Pro Val
             20                  25                  30 aag ccc ggc ccg gct ctc agc tac ccg cag gag gag gcc acc ctc aat       144
Lys Pro Gly Pro Ala Leu Ser Tyr Pro Gln Glu Glu Ala Thr Leu Asn
         35                  40                  45 gag atg ttc cgc gag gtt gag gaa ctg gtg gag gac acg cag cac aaa       192
Glu Met Phe Arg Glu Val Glu Glu Leu Val Glu Asp Thr Gln His Lys
     50                  55                  60 ttg cgc agc gcg gtg gaa gag atg gag gca gaa gaa gct gct gct aaa       240
Leu Arg Ser Ala Val Glu Glu Met Glu Ala Glu Glu Ala Ala Ala Lys
 65                  70                  75                  80 gca tca tca gaa gtg aac ctg gca aac tta cct ccc agc tat cac aat       288
Ala Ser Ser Glu Val Asn Leu Ala Asn Leu Pro Pro Ser Tyr His Asn
                 85                  90                  95 gag acc aac aca gac acg aag gtt gga aat aat acc atc cat gtg cac       336
Glu Thr Asn Thr Asp Thr Lys Val Gly Asn Asn Thr Ile His Val His
            100                 105                 110 cga gaa att cac aag ata acc aac aac cag gct cga caa atg gtc ttt       384
Arg Glu Ile His Lys Ile Thr Asn Asn Gln Ala Arg Gln Met Val Phe
        115                 120                 125
```

| | | | | | | | | | | | | | | | |
|---|---|---|---|---|---|---|---|---|---|---|---|---|---|---|---|
| tca | gag | aca | gtt | atc | aca | tct | gtg | gga | gac | gaa | gaa | ggc | aga | agg | agc | 432 |
| Ser | Glu | Thr | Val | Ile | Thr | Ser | Val | Gly | Asp | Glu | Glu | Gly | Arg | Arg | Ser | |
| | 130 | | | | 135 | | | | 140 | | | | | | | |

```
tca gag aca gtt atc aca tct gtg gga gac gaa gaa ggc aga agg agc      432
Ser Glu Thr Val Ile Thr Ser Val Gly Asp Glu Glu Gly Arg Arg Ser
    130             135             140 cac gag tgc atc atc gac gag gac tgt ggg ccc agc atg tac tgc cag      480
His Glu Cys Ile Ile Asp Glu Asp Cys Gly Pro Ser Met Tyr Cys Gln
145             150             155             160 ttt gcc agc ttc cag tac acc tgc cag cca tgc cgg ggc cag agg atg      528
Phe Ala Ser Phe Gln Tyr Thr Cys Gln Pro Cys Arg Gly Gln Arg Met
            165             170             175 ctc tgc acc cgg gac agt gag tgc tgt gga gac cag ctg tgt gtc tgg      576
Leu Cys Thr Arg Asp Ser Glu Cys Cys Gly Asp Gln Leu Cys Val Trp
        180             185             190 ggt cac tgc acc aaa atg gcc acc agg ggc agc aat ggg acc atc tgt      624
Gly His Cys Thr Lys Met Ala Thr Arg Gly Ser Asn Gly Thr Ile Cys
    195             200             205 gac aac cag agg gac tgc cag ccg ggg ctg tgc tgt gcc ttc cag aga      672
Asp Asn Gln Arg Asp Cys Gln Pro Gly Leu Cys Cys Ala Phe Gln Arg
210             215             220 ggc ctg ctg ttc cct gtg tgc ata ccc ctg ccc gtg gag ggc gag ctt      720
Gly Leu Leu Phe Pro Val Cys Ile Pro Leu Pro Val Glu Gly Glu Leu
225             230             235             240 tgc cat gac ccc gcc agc cgg ctt ctg gac ctc atc acc tgg gag cta      768
Cys His Asp Pro Ala Ser Arg Leu Leu Asp Leu Ile Thr Trp Glu Leu
            245             250             255 gag cct gat gga gcc ttg gac cga tgc cct tgt gcc agt ggc ctc ctc      816
Glu Pro Asp Gly Ala Leu Asp Arg Cys Pro Cys Ala Ser Gly Leu Leu
        260             265             270 tgc cag ccc cac agc cac agc ctg gtg tat gtg tgc aag ccg acc ttc      864
Cys Gln Pro His Ser His Ser Leu Val Tyr Val Cys Lys Pro Thr Phe
    275             280             285 gtg ggg agc cgt gac caa gat ggg gag atc ctg ctg ccc aga gag gtc      912
Val Gly Ser Arg Asp Gln Asp Gly Glu Ile Leu Leu Pro Arg Glu Val
290             295             300 ccc gat gag tat gaa gtt ggc agc ttc atg gag gag gtg cgc cag gag      960
Pro Asp Glu Tyr Glu Val Gly Ser Phe Met Glu Glu Val Arg Gln Glu
305             310             315             320 ctg gag gac ctg gag agg agc ctg act gaa gag atg gcg ctg ggg gag      1008
Leu Glu Asp Leu Glu Arg Ser Leu Thr Glu Glu Met Ala Leu Gly Glu
            325             330             335 cct gcg gct gcc gcc gct gca ctg ctg gga ggg gaa gag att tag          1053
Pro Ala Ala Ala Ala Ala Leu Leu Gly Gly Glu Glu Ile
        340             345             350

<210> SEQ ID NO 2
<211> LENGTH: 350
<212> TYPE: PRT
<213> ORGANISM: Homo sapiens

<400> SEQUENCE: 2

Met Gln Arg Leu Gly Ala Thr Leu Leu Cys Leu Leu Leu Ala Ala Ala
1               5                   10                  15

Val Pro Thr Ala Pro Ala Pro Ala Pro Thr Ala Thr Ser Ala Pro Val
            20                  25                  30

Lys Pro Gly Pro Ala Leu Ser Tyr Pro Gln Glu Glu Ala Thr Leu Asn
        35                  40                  45

Glu Met Phe Arg Glu Val Glu Glu Leu Val Glu Asp Thr Gln His Lys
    50                  55                  60

Leu Arg Ser Ala Val Glu Glu Met Glu Ala Glu Ala Ala Lys
65                  70                  75                  80
```

```
Ala Ser Ser Glu Val Asn Leu Ala Asn Leu Pro Pro Ser Tyr His Asn
             85                  90                  95
Glu Thr Asn Thr Asp Thr Lys Val Gly Asn Asn Thr Ile His Val His
        100                 105                 110
Arg Glu Ile His Lys Ile Thr Asn Asn Gln Ala Arg Gln Met Val Phe
    115                 120                 125
Ser Glu Thr Val Ile Thr Ser Val Gly Asp Glu Gly Arg Arg Ser
130                 135                 140
His Glu Cys Ile Ile Asp Glu Asp Cys Gly Pro Ser Met Tyr Cys Gln
145                 150                 155                 160
Phe Ala Ser Phe Gln Tyr Thr Cys Gln Pro Cys Arg Gly Gln Arg Met
                165                 170                 175
Leu Cys Thr Arg Asp Ser Glu Cys Cys Gly Asp Gln Leu Cys Val Trp
            180                 185                 190
Gly His Cys Thr Lys Met Ala Thr Arg Gly Ser Asn Gly Thr Ile Cys
        195                 200                 205
Asp Asn Gln Arg Asp Cys Gln Pro Gly Leu Cys Cys Ala Phe Gln Arg
    210                 215                 220
Gly Leu Leu Phe Pro Val Cys Ile Pro Leu Pro Val Glu Gly Glu Leu
225                 230                 235                 240
Cys His Asp Pro Ala Ser Arg Leu Leu Asp Leu Ile Thr Trp Glu Leu
                245                 250                 255
Glu Pro Asp Gly Ala Leu Asp Arg Cys Pro Cys Ala Ser Gly Leu Leu
            260                 265                 270
Cys Gln Pro His Ser His Ser Leu Val Tyr Val Cys Lys Pro Thr Phe
        275                 280                 285
Val Gly Ser Arg Asp Gln Asp Gly Glu Ile Leu Leu Pro Arg Glu Val
    290                 295                 300
Pro Asp Glu Tyr Glu Val Gly Ser Phe Met Glu Glu Val Arg Gln Glu
305                 310                 315                 320
Leu Glu Asp Leu Glu Arg Ser Leu Thr Glu Glu Met Ala Leu Gly Glu
                325                 330                 335
Pro Ala Ala Ala Ala Ala Ala Leu Leu Gly Gly Glu Glu Ile
            340                 345                 350

<210> SEQ ID NO 3
<211> LENGTH: 117
<212> TYPE: DNA
<213> ORGANISM: Homo sapiens

<400> SEQUENCE: 3
atgcagcggc ttggggccac cctgctgtgc ctgctactgg cggcggcggt ccccacggcc      60
cccgcgcccg ctccgacggc gacctcggct ccagtcaagc ccggcccggc tctcagc       117

<210> SEQ ID NO 4
<211> LENGTH: 234
<212> TYPE: DNA
<213> ORGANISM: Homo sapiens

<400> SEQUENCE: 4
atgcagcggc ttggggccac cctgctgtgc ctgctactgg cggcggcggt ccccacggcc      60
cccgcgcccg ctccgacggc gacctcggct ccagtcaagc ccggcccggc tctcagctac     120
ccgcaggagg aggccaccct caatgagatg ttccgcgagg ttgaggaact ggtgggggac     180
acgcagcaca aattgcgcag cgcggtggaa gagatggagg cagaagaagc tgct           234
```

<210> SEQ ID NO 5
<211> LENGTH: 262
<212> TYPE: DNA
<213> ORGANISM: Artificial
<220> FEATURE:
<223> OTHER INFORMATION: Synthetic

<400> SEQUENCE: 5

```
tgactgactg acgtttaaac ccgctgatca gcctcgactg tgccttctag ttgccagcca      60
tctgttgttt gccccteccc cgtgccttcc ttgaccctgg aaggtgccac tcccactgtc     120
ctttcctaat aaaatgagga aattgcatcg cattgtctga gtaggtgtca ttctattctg     180
gggggtgggg tggggcagga cagcaagggg gaggattggg aagacaatag caggcatgct     240
ggggatgcgg tgggctctat gg                                              262
```

<210> SEQ ID NO 6
<211> LENGTH: 2355
<212> TYPE: DNA
<213> ORGANISM: Artificial
<220> FEATURE:
<223> OTHER INFORMATION: Synthetic

<400> SEQUENCE: 6

```
tctagagcac catgcagcgg cttggggcca ccctgctgtg cctgctgctg gcggcggcgg      60
tccccacggc ccccgcgccc gctccgacgg cgacctcggc tccagtcaag cccggccgg     120
ctctcagcta cccgcaggag gaggccaccc tcaatgagat gttccgcgag gttgaggaac     180
tgatggagga cacgcagcac aaattgcgca gcgcggtgga agagatggag gcagaagaag     240
ctgctgctaa agcatcatca gaagtgaacc tggcaaactt acctcccagc tatcacaatg     300
agaccaacac agacacgaag gttggaaata ataccatcca tgtgcaccga gaaattcaca     360
agataaccaa caaccagact ggacaaatgg tcttttcaga cacagttatc acatctgtgg     420
gagacgaaga aggcagaagg agccacgagt gcatcatcga cgaggactgt gggcccagca     480
tgtactgcca gtttgccagc ttccagtaca cctgccagcc atgccggggc cagaggatgc     540
tctgcacccg ggacagtgag tgctgtggag accagctgtg tgtctgggt cactgcacca     600
aaatggccac caggggcagc aatgggacca tctgtgacaa ccagagggac tgccagccgg     660
ggctgtgctg tgccttccag agaggcctgc tgttccctgt gtgcacaccc ctgcccgtgg     720
agggcgagct ttgccatgac cccgccagcc ggcttctgga cctcatcacc tgggagctag     780
agcctgatgg agccttggac cgatgccctt gtgccagtgg cctcctctgc cagccccaca     840
gccacagcct ggtgtatgtg tgcaagccga ccttcgtggg gagccgtgac caagatgggg     900
agatcctgct gcccagagag gtccccgatg agtatgaagt tggcagcttc atggaggagg     960
tgcgccagga gctggaggac ctggagagga gcctgactga agagatggcg ctggggagc    1020
ctgcggctgc cgccgctgca ctgctgggag gggaagagat ttaggggta ccccggctag    1080
atgactaacg tttaaacccg ctgatcagcc tcgactgtgc cttctagttg ccagccatct    1140
gttgtttgcc ctcccccgt gccttccttg accctggaag gtgccactcc cactgtcctt    1200
tcctaataaa atgaggaaat tgcatcgcat tgtctgagta ggtgtcattc tattctgggg    1260
ggtggggtgg ggcaggacag caaggggag gattgggaag acaatagcag gcatgctggg    1320
gatgcggtgg gctctatggc ggagtactgt cctccgcttc ccacgtgcg gagggactgg    1380
ggacccgggc accgtcctg cccttcacc ttcagctcc gctcctccg cgcggacccc       1440
gccccgtccc gaccctccc gggtcccgg cccagccccc tcgggccct cccagcccct       1500
```

```
cccccttcctt tccgcggccc cgccctctcc tcgcggcgcg agttttggaa agtccccagg    1560
ctccccagca ggcagaagta tccaaagcat ccatctcaat tagtcagcaa ccaggtgtgg    1620
aaagtcccca ggctccccag caggcagaag tatccaaagc atccatctca attagtcagc    1680
aaccatagtc ccgcccctaa ctccgcccat cccgccccta actccgccca gttccgccca    1740
ttctccgccc catggctgac taatttttt tatttatgca gaggccgagg ccgcctctgc    1800
ctctgagcta ttccagaagt agtgaggagg ctttttga ggccaaggct tttgcaaaaa    1860
gctccgttac ataacttacg gtaaatggcc cgcctggctg accgcccaac gaccccgcc    1920 cattgacgtc aataatgacg tatgttccca tagtaacgcc aatagggact tccattgac    1980 gtcaatgggt ggagtattta cggtaaactg cccacttggc agtacatcaa gtgtatcata    2040
tgccaagtac gccccctatt gacgtcaatg acggtaaatg gccgcctgg cattatgccc    2100 agtacatgac cttatgggac tttcctactt ggcagtacat ctacgtatta gtcatcgcta    2160
ttaccatggt gatgcggttt tggcagtaca tcaatgggcg tggatagcgg tttgactcac    2220
ggggatttcc aagtctccac cccattgacg tcaatgggag tttgttttgg caccaaaatc    2280
aacgggactt tccaaaatgt cgtaacaact ccgccccatt gacgcaaatg ggcggtaggc    2340
gtgttgccgg aattc                                                    2355

<210> SEQ ID NO 7
<211> LENGTH: 1285
<212> TYPE: DNA
<213> ORGANISM: Artificial
<220> FEATURE:
<223> OTHER INFORMATION: Synthetic

<400> SEQUENCE: 7
gtttaaaccc gctgatcagc ctcgactgtg ccttctagtt gccagccatc tgttgtttgc      60
ccctcccccg tgccttcctt gaccctggaa ggtgccactc ccactgtcct ttcctaataa     120
aatgaggaaa ttgcatcgca ttgtctgagt aggtgtcatt ctattctggg gggtggggtg     180
gggcaggaca gcaaggggga ggattgggaa gacaatagca ggcatgctgg ggatgcggtg     240
ggctctatgg cggagtactg tcctccgctt cccacgtggc ggagggactg gtcctccgct     300
tcccacgtgg cggagggact ggggacccgg gcacccgtcc tgcccttca ccttccagct     360 ccgcctcctc cgcgcggacc ccgccccgtc ccgaccctc ccgggtcccc ggcccagccc     420
cctccgggcc ctcccagccc ctccccttcc tttccgcggc cccgccctct cctcgcggcg     480 cgagtttttgg aaagtcccca ggctccccag caggcagaag tatccaaagc atccatctca     540
attagtcagc aaccaggtgt ggaaagtccc caggctcccc agcaggcaga agtatccaaa     600
gcatccatct caattagtca gcaaccatag tcccgcccct aactccgccc atcccgcccc     660
taactccgcc cagttccgcc cattctccgc cccatggctg actaatttt tttatttatg     720 cagaggccga ggccgcctct gcctctgagc tattccagaa gtagtgagga ggcttttttg     780
gaggccaagg cttttgcaaa aagctccgtt acataactta cggtaaatgg cccgcctggc     840
tgaccgccca acgacccccg cccattgacg tcaataatga cgtatgttcc catagtaacg     900
ccaataggga ctttccattg acgtcaatgg gtggagtatt tacggtaaac tgcccacttg     960
gcagtacatc aagtgtatca tatgccaagt acgcccccta ttgacgtcaa tgacggtaaa    1020
tggcccgcct ggcattatgc ccagtacatg accttatggg actttcctac ttggcagtac    1080
atctacgtat tagtcatcgc tattaccatg gtgatgcggt tttggcagta catcaatggg    1140
```

-continued

```
cgtggatagc ggtttgactc acggggattt ccaagtctcc accccattga cgtcaatggg      1200
agtttgtttt ggcaccaaaa tcaacgggac tttccaaaat gtcgtaacaa ctccgcccca      1260
ttgacgcaaa tgggcggtag gcgtg                                            1285
```

```
<210> SEQ ID NO 8
<211> LENGTH: 21
<212> TYPE: DNA
<213> ORGANISM: Artificial
<220> FEATURE:
<223> OTHER INFORMATION: Primer

<400> SEQUENCE: 8
atgagacata ttatctgcca c                                                  21

<210> SEQ ID NO 9
<211> LENGTH: 22
<212> TYPE: DNA
<213> ORGANISM: Artificial
<220> FEATURE:
<223> OTHER INFORMATION: Primer

<400> SEQUENCE: 9
gtaagtcaat cccttcctgc ac                                                 22
```